(12) United States Patent
Kansal et al.

(10) Patent No.: US 7,687,660 B2
(45) Date of Patent: Mar. 30, 2010

(54) PROCESS FOR PREPARING INTERMEDIATES OF HMG-COA REDUCTASE INHIBITORS

(75) Inventors: Vinod Kumar Kansal, Faridabad (IN); Brijnath P. Chaurasia, Ballia (IN); Hitesh K. Patel, Vadodara (IN); Vrajlal Gothalia, Amnagar (IN); Hiren Gandhi, Navsari (IN)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 0 days.

(21) Appl. No.: 12/148,533

(22) Filed: Apr. 18, 2008

(65) Prior Publication Data

US 2009/0076271 A1 Mar. 19, 2009

Related U.S. Application Data

(60) Provisional application No. 60/925,216, filed on Apr. 18, 2007, provisional application No. 60/931,926, filed on May 24, 2007, provisional application No. 61/066,678, filed on Feb. 21, 2008, provisional application No. 61/069,099, filed on Mar. 11, 2008.

(51) Int. Cl.
C07C 229/00 (2006.01)
(52) U.S. Cl. .................................... 560/170
(58) Field of Classification Search ........... None
See application file for complete search history.

(56) References Cited

U.S. PATENT DOCUMENTS

| | | | |
|---|---|---|---|
| 5,260,440 A | 11/1993 | Hirai et al. | |
| 5,354,879 A | 10/1994 | Konoike et al. | |
| RE37,314 E | 8/2001 | Hirai et al. | |
| 6,777,552 B2 | 8/2004 | Niddam-Hildesheim et al. | |
| 6,909,003 B2 | 6/2005 | Storz | |
| 7,208,623 B2 | 4/2007 | Sedelmeier et al. | |
| 2005/0070605 A1 | 3/2005 | Acemoglu et al. | |
| 2007/0099994 A1 | 5/2007 | Niddam-Hildesheim et al. | |
| 2009/0076292 A1 | 3/2009 | Kansal et al. | |

FOREIGN PATENT DOCUMENTS

| | | |
|---|---|---|
| CN | 1807417 | 7/2006 |
| CN | 1821242 | 8/2006 |
| CN | 1307187 C | 3/2007 |
| CN | 1958593 | 5/2007 |
| CZ | 298330 | 8/2007 |
| EP | 0 521 471 | 1/1993 |
| EP | 1 634 870 | 3/2006 |
| WO | WO 03/087112 | 10/2003 |
| WO | WO 03/097614 | 11/2003 |
| WO | WO 2006/021326 | 3/2006 |
| WO | WO 2006/091771 | 8/2006 |
| WO | WO 2007/041666 | 4/2007 |

OTHER PUBLICATIONS

Theisen et al, The Journal of Organic Chemistry, Improved Procedure for Preparation of Optically Active 3-Hydroxyglutarate Monoesters and 3-Hydroxy-5-alkanoic Acids, 1988, 53 (10), pp. 2374-2378.*
Greene, Protective Groups in Organic Chemistry, John Wiley & Sons, Inc., New York, pp. 158-159, 168-169.*
Heathcock, C.H. et al., "Total synthesis and biological evaluation of structural analogs of compactin and dihydromevinolin," *Journal of Medicinal Chemistry*, vol. 30(10), 1987: 1858-1873.
Helvetica Chimica Acta, vol. 90 (2007).
Karanewsky, D.S. et al., "Practical synthesis of an enantiomerically pure synthon for the preparation of mevinic acid analogs," *Journal of Organic Chemistry*, vol. 56(11), 1991: 3744-3747.
Rosen, T. et al., "Total synthesis of dextro compactin," *Journal of the American Chemical Society*, vol. 107(12), 1985: 3731-3733.
Sunazuka, T. et al., "Total synthesis of pinellic acid, a potent oral adjuvant for nasal influenza vaccine. Determination of the relative and absolute configuration," *Tetrahedron Letters*, vol. 43(7), 2002: 1265-1268.
Theisen, P.D. et al., "Improved procedure for preparation of optically active 3-hydroxyglutarate monoesters and 3-hydroxy-5-oxoalkanoic acids," *Journal of Organic Chemistry*, vol. 53(10), 1988: 2374-2378.
Watanabe, et al., "Synthesis and Biological Antivity Of Methanesulfonamide Pyramidine-And N-Methanesulfonyl Pyrrole-Substituted 3,5-Dihydroxy-6-Heptenoates, A Novel Series Of HMG-CoA Reductase Inhibitors", *Bioorganic & Medicinal Chemistry*, 1997, pp. 437-444, vol. 5, No. 2.

* cited by examiner

*Primary Examiner*—Paul A Zucker
(74) *Attorney, Agent, or Firm*—Kenyon & Kenyon LLP

(57) ABSTRACT

The present invention relates to intermediates of rosuvastatin and processes for the production thereof.

15 Claims, No Drawings

PROCESS FOR PREPARING INTERMEDIATES OF HMG-COA REDUCTASE INHIBITORS

CROSS-REFERENCE TO RELATED APPLICATIONS

This application claims the benefit of U.S. Provisional Application No. 60/925,216, filed Apr. 18, 2007; 60/931,926, filed May 24, 2007; 61/066,678, filed Feb. 21, 2008, and 61/069,099, filed Mar. 11, 2008. The contents of which are incorporated herein by reference.

FIELD OF THE INVENTION

The invention relates to rosuvastatin intermediates and processes for their preparation thereof.

BACKGROUND OF THE INVENTION

Rosuvastatin (7-[4-(4-fluorophenyl)-6-isopropyl-2-(N-methyl-N-methylsulfonylamino) pyrimidin-5-yl]-(3R,5S)-dihydroxy-(E)-6-heptenoic acid) calcium is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium has the following chemical formula:

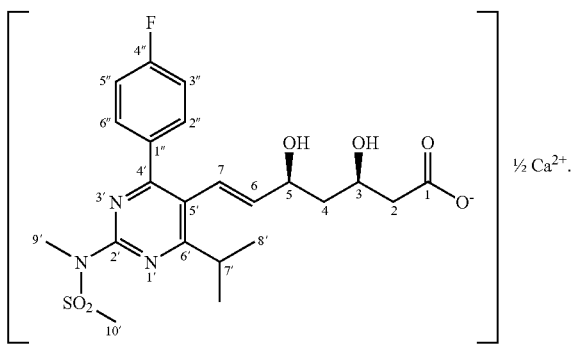

Rosuvastatin calcium is marketed under the name CRESTOR for treatment of a mammal such as a human. According to the maker of CRESTOR, it is administered in a daily dose of from about 5 mg to about 40 mg for LDL cholesterol reduction.

U.S. Pat. No. 5,260,440 (EP0521471A1) (US '440), discloses the synthesis of rosuvastatin from the intermediate 3(R)-3(tert-butyldimethylsilyloxy)-5-oxo-6-triphenyl-phoporanylidene hexanoate. PCT publication No. WO 03/097614 discloses the synthesis of rosuvastatin from the intermediate (3R)-3-(tert-butyldimethylsilyloxy)-5-oxo-6-triphenyl-phosphoralydene hexanoate, disclosed in US '440 patent.

PCT publication No. WO 03/087112 discloses the synthesis of rosuvastatin from a different intermediate, (3R)-3-(t-butyldimethylsilyloxy)-6-dimethoxyphosphinyl-5-oxohexanate (TSPH), which was synthesized from 3-hydroxy diethyl glutarate via partial hydrolysis by a microorganism to obtain enantiomerically pure glutaric acid derivative according to Scheme 1:

Scheme 1

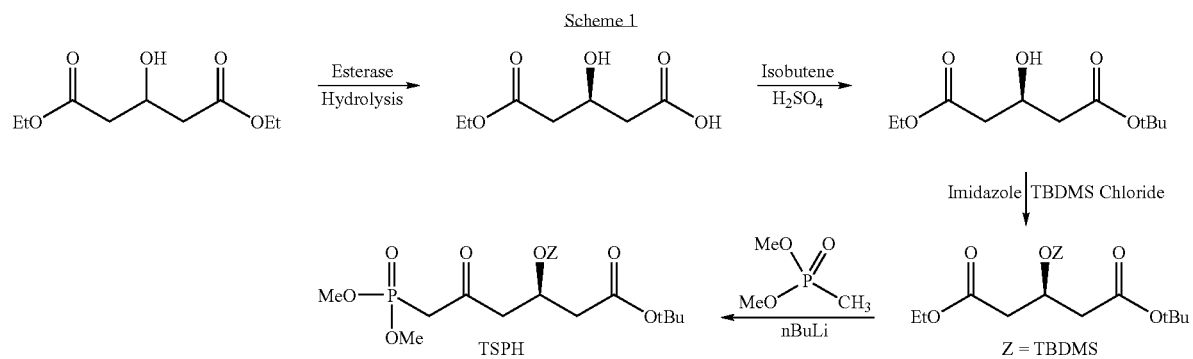

The process of PCT publication No. WO 03/087112 may not be desirable on an industrial scale. For example, it requires the use of an expensive microorganism such as CLS-BC-14011 during the partial hydrolysis of 3-hydroxy diethyl glutarate. Additionally, the process uses a hazardous reaction, such as isobutylene gas during esterification of ethyl-(3S)-3-hydroxyglutaric acid in the presence of sulphuric acid, and the purification of TSPH by column chromatography is commercially difficult.

US publication No. 2005/0070605A1 discloses the enantioselective opening of 3-hydroxyprotected glutaric anhydride by phenyl ethylamine to form an amide bond, and further converting it to HMG-CoA reductase inhibitor. The process may have problems such as breaking of the phenyl ethyl amide bond in the final step of producing cerivastatin and the problematic removal of phenylethylamine after breaking of the amide linkage in the synthesis of pitavastatin.

PCT publication No. WO 2006/021326 discloses the opening of 3-hydroxy protected glutaric anhydride by methanol to yield racemic methyl 3(±)-3-(t-butyl dimethylsilyloxy)-6-dimethoxy-phosphinyl-5-oxohexante, and the preparation of racemic methyl (3R)-3-(t-butyl dimethylsilyloxy)-6-dimethoxy-phosphinyl-5-oxohexante.

U.S. Pat. No. 5,354,879 discloses the preparation of both methyl (3R)-3-(t-butyl dimethylsilyloxy)-6-dimethoxyphosphinyl-5-oxohexante and 3(R)-3(tert-butyldimethylsilyloxy)-5-oxo-6-triphenyl-phoporanylidene hexanoate from (3R) 3-[(tert-butyldimethylsilyl)oxy]-glutaric acid 1-(R)-(−)-mandelate and (3S) 3-[(tert-butyldimethylsilyl)oxy]-glutaric acid 1-(S)-(+)-mandelate, respectively. The disclosed process employs explosive and toxic materials, such as diazomethane, during the preparation of methyl-(3R)-3-(t-butyl dimethylsilyloxy)-6-dimethoxy-phosphinyl-5-oxohexante (esterification). Moreover, the yield of the above steps is low, and thus the process may not suitable for industrial and commercial use.

J. Org. Chem. (1991) 56:3744-47 discloses the preparation of (3R)-3-(t-butyl dimethylsilyloxy)-6-dimethoxy-phosphinyl-5-oxohexante from 3-hydroxy protected glutaric anhydride. The disclosed process which involves using hazardous reactions, such as use of $N_2O_4$ oxidation, followed by a hydrogenation reaction to cleave the amino group of the resolving agent, and use of diazomethane. The process also uses an expensive palladium catalyst which could remain as an impurity in the final product.

SUMMARY OF THE INVENTION

In one embodiment, the present invention provides a process for preparing a compound of formula 4, having the following structure:

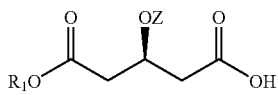

4 by enantioselectively opening the prochiral anhydride compound of formula 3, having the following structure:

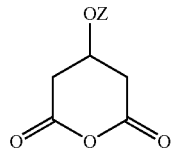

3 using $C_1$-$C_5$ alcohol in the presence of alkaloid, wherein $R_1$ is $C_1$-$C_5$ alkyl preferably $C_1$-$C_4$; and Z is a hydroxy protecting group. The protecting group is preferably a silyl group, including trialkylsilysl group having the formula-Si(A)$_3$ where each A is independently selected from a $C_1$-$C_6$ linear or branched aliphatic or aromatic group. Examples of silyl groups include triethylsilyl, triisopropylsilyl, tert-butyldiphenylsilyl, tert-butyldimethylsilyl. Preferably the silyl group is tert-butyldimethylsilyl.

In another embodiment, the present invention further provides a process for preparing the compound of formula 5 having the following structure:

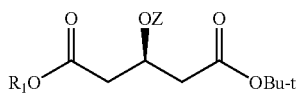

5 by combining the compound of formula 4, described above, with BOC anhydride in the presence of a basic catalyst, wherein $R_1$ is $C_1$-$C_5$ alkyl, preferably $C_1$-$C_4$; and Z is a hydroxy protecting group as above.

The compound of formula 5, described above, is selectively hydrolyzed to obtain the compound of formula 6.

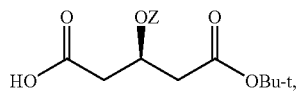

6 wherein Z is a hydroxy protecting group as above.

The compound of formula 6 may be used to prepare the compound of formula 2, having the following structure:

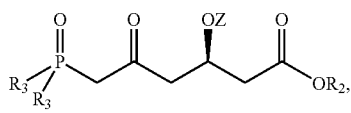

2 wherein $R_2$ is methyl, ethyl, or t-butyl; Z is a hydroxy protecting group as above; and $R_3$ is $C_1$ to $C_3$ alkoxy, $C_6$ to $C_{12}$ aryloxy, or substituted aryloxy.

In yet another embodiment, the present invention provides a process for preparing a compound of formula 7, having the following structure:

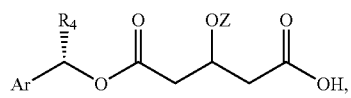

7 by enantioselectively opening the prochiral anhydride of formula 3, having the following structure:

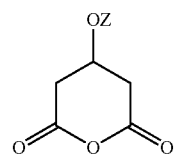

3 using a chiral alcohol of the formula 3a, having the following structure:

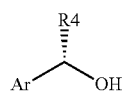

3a wherein $R_4$ is $C_1$ to $C_6$ alkyl, e.g., methyl or ethyl, and Ar is phenyl or substituted phenyl, and Z is a hydroxy protecting group as above.

In one embodiment, the present invention provides a compound of formula 7 having the following structure:

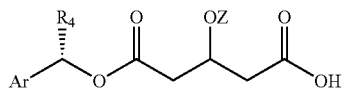

7 wherein $R_4$ is $C_1$ to $C_6$ alkyl, e.g., methyl or ethyl, Ar is phenyl or substituted phenyl, and Z is a hydroxy protecting group as above. Also provided is a compound of formula 7 which is at least 50% chiral pure. Optionally, the compound of formula 7 can be purified by HPLC. The enriched enantiomer has the following structure;

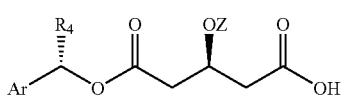

7a

In another embodiment, the present invention provides a compound of formula 8 having the following structure:

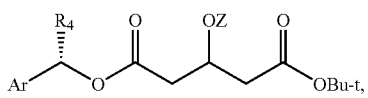

8 wherein Z is a hydroxy protecting group as above, $R_4$ is $C_1$ to $C_6$ alkyl, e.g., methyl or ethyl, and Ar is phenyl or substituted phenyl. Also provided is a compound of formula 8 which is at least 50% chiral pure. Optionally, the compound of formula 8 can be purified by HPLC. The enriched enantiomer has the following structure;

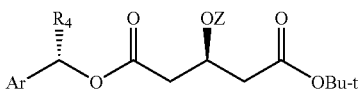

8a

In yet another embodiment, the present invention further provides a process for the preparation of the compound of formula 8, described above, by combining a compound of formula 7, described above, with BOC anhydride.

In one embodiment, the present invention provides a process for preparing a compound of formula 6, having the following structure:

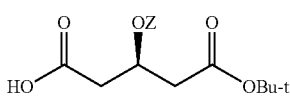

6 by selectively hydrolyzing the compound of formula 8, wherein Z is a hydroxy protecting group as above.

In another embodiment, the present invention provides a process for preparing the compound of formula 4a, having the following structure:

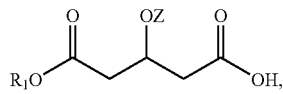

4a by enantioselectively opening the prochiral anhydride compound of formula 3, described above, by combining it with $C_1$-$C_5$ alkyl alcohols in the presence of alkaloids, wherein Z is a hydroxy protecting group as above and $R_1$ is lower alkyl, preferably $C_1$ to $C_4$ carbon. The enriched enantiomer has the following structure;

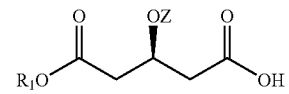

4

In yet another embodiment, the present invention provides a process for preparing compound of formula 5a, having the following structure:

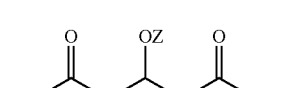

5a by combining the compound of formula 4a, described above with BOC anhydride in the presence of a base, wherein Z is a hydroxy protecting group as above and $R_1$ is $C_1$ to $C_5$ alkyl, preferably $C_1$ to $C_4$ alkyl. The enriched enantiomer has the following structure;

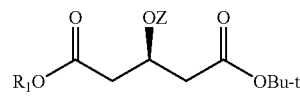

5

In one embodiment, the present invention provides a process for preparing compound of formula 6a, having the following structure:

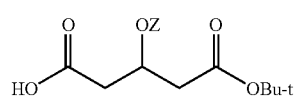

6a by selectively hydrolyzing the compound of formula 5a, described above, wherein Z is a hydroxy protecting group as above. The enriched enantiomer has the following structure;

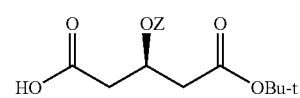

6

In another embodiment, the present invention provides a compound of formula 7 having the following structure:

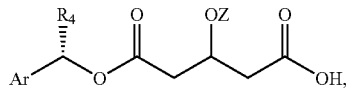

wherein $R_4$ is $C_1$ to $C_6$ alkyl, e.g., methyl or ethyl, Ar is phenyl or substituted phenyl, and Z is a hydroxy protecting group as above.

In yet another embodiment, the present invention also provides a process for preparing the compound of formula 7a by enantioselectively opening the prochiral anhydride of formula 3, described above with chiral alcohols of the formula 3a, described above, wherein $R_4$ is $C_1$ to $C_6$ alkyl, e.g., methyl or ethyl, Ar is phenyl or substituted phenyl, and Z is a hydroxy protecting group as above. The enriched enantiomer of formula 7 has the following structure;

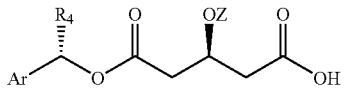

In one embodiment, the invention provides a compound of formula 8 having the following structure:

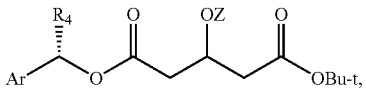

wherein Z is a hydroxy protecting group as above and $R_4$ is $C_1$ to $C_6$ alkyl. The enriched enantiomer of formula 8 has the following structure;

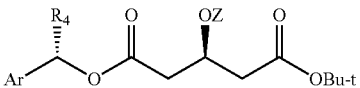

In another embodiment, the present invention also provides a process for preparing the compound of formula 8a by combining the compound of formula 7a, described above, with BOC anhydride in the presence of a base.

In yet another embodiment, the present invention also provides a process for preparing compound of formula 6a having the following structure:

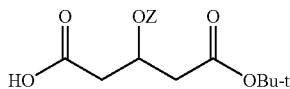

by selectively hydrolyzing the compound of formula 8a, described above, wherein Z is a hydroxy protecting group as above. The enriched enantiomer of formula 6a has the following structure;

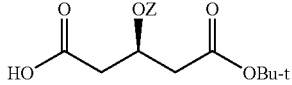

In one embodiment, the present invention also provides a process for preparing the chiral pure R-isomer compound of formula 6, described above, by an optical resolution process by combining the compound of formula 6a, described above, a compound (R)-(+)-phenylethylamine of formula 9a, having the following structure:

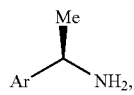

or a compound (S)-(−)-phenylethylamine of formula 9b, having the following structure:

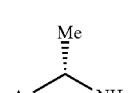

In another embodiment, the present invention provides a compound of formula 9, having the following structure:

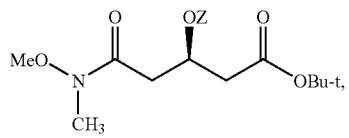

wherein Z is a hydroxy protecting group as above.

In yet another embodiment, the present invention also provides a process for preparing the compound of formula 9 by combining the compound of formula 6, described above, with at least one organic solvent, preferably selected from the group consisting of: $C_5$-$C_{12}$ aromatic hydrocarbons optionally substituted with halogen, —SH, —OH, —$NO_2$, or —$NH_2$; $C_5$-$C_{12}$ aromatic hydrocarbons where one or more ring carbons is substituted with N, S, or O; $C_6$-$C_{10}$ aliphatic hydrocarbons, halogenated $C_1$-$C_{12}$ hydrocarbons, ethers and ketones, an amidation reagent selected from the group consisting of: $C_{1-4}$ alkyl and $C_{6-8}$ aryl haloformates and acid halides, and at least one base; and adding N,O-dimethyl hydroxylamine.

In one embodiment, the present invention provides a novel process for the preparation of a chirally pure compound of the general formula A, having the following structure:

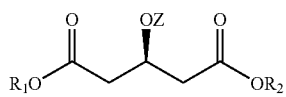

wherein $R_1$ is H, $C_1$-$C_5$ alkyl, or a $C_1$ to $C_5$-carbonyl; $R_2$ is $C_1$-$C_6$ alkyl, e.g., methyl, ethyl, or t-butyl group; and Z is a hydroxy protecting group. The protecting group is preferably a silyl group, including trialkylsilysl group having the formula-Si(A)₃ where each A is independently selected from a $C_1$-$C_6$ linear or branched aliphatic or $C_5$-$C_{12}$ aromatic group. Examples of silyl groups include trimethylsilyl, triethylsilyl, triisopropylsilyl, tert-butyldiphenylsilyl, tert-butyldimethylsilyl, methyldiphenylsilyl, and dimethylphenylsilyl. Preferably the silyl group is tert-butyldimethylsilyl. Preferably, $R_2$ is t-butyl group.

In another embodiment, the present invention provides a process for preparing a compound of formula 2, having the following structure:

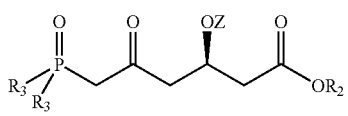

2 by combining the compound of formula 9, described above with a lithiated salt of dialkyl phosphonate, wherein $R_3$ is $C_1$ to $C_3$ alkyloxy, $C_5$-$C_{12}$ aryloxy, substituted $C_5$-$C_{12}$ aryloxy and Z is a hydroxy protecting group as above

DETAILED DESCRIPTION OF THE INVENTION

The substituents in the "substituted alkyl" or "substituted aryl or phenyl" may be selected from the groups such as hydroxy, carboxyl, alkyl (such as $C_1$-$C_4$), alkoxy (such as $C_6$-$C_{12}$), aryl (such as $C_6$-$C_{12}$), arylalkyl (such as $C_6$-$C_{12}$), cycloalkyl (such as $C_6$-$C_{12}$) and amino. When an aromatic solvent is used, the solvent can be substituted with halogen (such as chlorine), —SH, —OH, —NO₂, or —NH₂.

The invention provides a process for producing chirally pure (more than 50% enrichment) compounds of formulas A and 2 in high yield, making the process economically attractive by using less toxic chemicals and fewer reaction steps.

The invention provides a process for preparing a compound of formula 4, having the following structure:

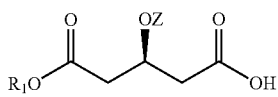

4 by enantioselectively opening the prochiral anhydride compound of formula 3, having the following structure:

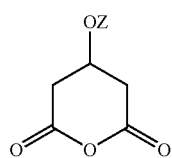

3 using $C_1$-$C_5$ alcohol of the formula $R_1$—OH in the presence of alkaloid, wherein $R_1$ is $C_1$-$C_5$ alkyl, preferably C1 to C4 alkyl, more preferably $R_1$ is a methyl group and Z is a hydroxy protecting group. The protecting group is preferably a silyl group, including trialkylsilysi group having the formula-Si (A)₃ where each A is independently selected from a $C_1$-$C_6$ linear or branched aliphatic or aromatic group. Examples of silyl groups include trimethylsilyl, triethylsilyl, triisopropylsilyl, tert-butyldiphenylsilyl, tert-butyldimethylsilyl, methyldiphenylsilyl, and dimethylphenylsilyl, preferably tert-butyldimethylsilyl.

Preferably, a $C_1$-$C_5$ alkyl alcohol is used in the presence of an alkaloid. Examples of alkaloids include a) Indole alkaloids such as 5-MeO-DMT, dimethyltryptamine, Harmala alkaloids, psilocin, psilocybin, reserpine, serotonin, tryptamine, yohimbine; b) phenethylamine alkaloids such as amphetamine, cathinone, ephedrine, mescaline, methamphetamine, phenethylamine, tyramine; c) purine alkaloids such as caffeine, theobromine, theophylline, d) pyridine alkaloids such as Coniine; d) pyrrolidine alkaloids such as nicotine e) quinoline alkaloids such as quinine or quinidin; and f) terpenoids such as aconitine and solanine. More preferably the akaloid is quinine or quinidine.

Preferably, the reaction temperature is between about −35° C. to about −60° C., more preferably, between about −40° C. to about −50° C. Preferably, the reaction is maintained for about 5 to about 30 hours, more preferably for about 12 to about 24 hours. Preferably the compound of formula 4 obtained is in enantiomeric excess of about 80% to about 98%, more preferably about 85% to about 90% as measured by chiral HPLC.

The present invention further provides a process for preparing the compound of formula 5 having the following structure:

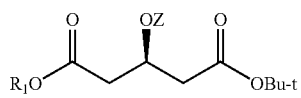

5 by combining the compound of formula 4, described above, with BOC anhydride (Di-tert-butyl dicarbonate) in the presence of a basic catalyst, wherein $R_1$ is $C_1$-$C_5$ alkyl group as described above; and Z is a hydroxy protecting group as described above.

The basic catalyst is preferably a tertiary amine such N-methyl morpholine, N,N-dimethylaminopyridine, and mixtures thereof. The tertiary amine base is of the formula N(A1)(A2)(A3), contains $C_3$-$C_{15}$ carbon atoms wherein A1, A2, and A3 are each independently selected from a $C_1$-$C_{10}$ alkyl group and a $C_5$-$C_{12}$ aromatic group, wherein A1, A2, and A3 can further include an oxygen or a nitrogen (such as cyclic structures like morpholino and pyridine groups). In one embodiment A1 and A2 are methyl groups, and A3 is a $C_5$-$C_{12}$ aromatic group containing a nitrogen or an oxygen (such as cyclic structures like morpholino and pyridine groups).

The protecting group is preferably a silyl group, including trialkylsilysl group having the formula-Si(A)₃ where each A is independently selected from a $C_1$-$C_6$ linear or branched aliphatic or $C_5$-$C_{12}$ aromatic group. Examples of silyl groups include trimethylsilyl, triethylsilyl, triisopropylsilyl, tert-butyldiphenylsilyl, tert-butyldimethylsilyl, methyldiphenylsilyl, and dimethylphenylsilyl. Preferably the silyl group is tert-butyldimethylsilyl.

The combination of compound of formula 4 with BOC anhydride in the presence of a base catalyst can be maintained at a temperature of about 5° C. to about 50° C., more preferably, at about 10° C. to about 30° C. The combination can be maintained for a period of about 2 to about 10 hours, more preferably about 2 to about 5 hours.

The compound of formula 5, described above, is selectively hydrolyzed to obtain the compound of formula 6.

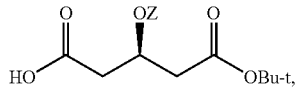

6 wherein Z is a hydroxy protecting group as described above.

The hydrolysis is carried out under basic conditions in an alcohol. The concentration of the alkaline solution can be about 0.5 to about 2N. The alcohol is can be a C1-C4 alcohol, preferably selected from the group consisting of: methyl alcohol, ethyl alcohol, and mixtures thereof, more preferably ethyl alcohol. The reaction can be maintained for a period of about 2 to about 12 hours, such as about 6 to about 8 hours. In one embodiment, the reaction is maintained at a temperature of about 20° C. to about 60° C., such as at about 45° C. to about 55° C. Examples of suitable bases include alkali metal and alkaline earth metal bases, particularly hydroxide bases such as sodium and potassium hydroxide. After the hydrolysis, the reaction mixture can be acidified. Compound of 6 can then be extracted into a water immiscible solvent such as toluene, followed by evaporation of the toluene, such as at a pressure of less than one atmosphere.

The invention provides a process for preparing a compound of formula 7, having the following structure:

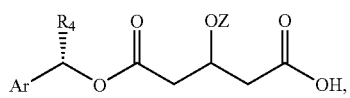

7 by enantioselectively opening the prochiral anhydride of formula 3, having the following structure:

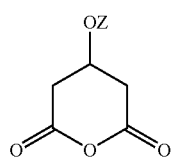

3 using a chiral alcohol of the formula 3a, having the following structure:

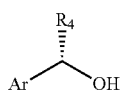

3a wherein $R_4$ is $C_1$-$C_6$ alkyl, e.g., methyl or ethyl, and Ar is phenyl or substituted phenyl as defined above, and Z is a hydroxy protecting group as above. The enriched enantiomer of formula 7 has the following structure;

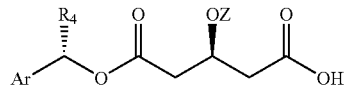

7a

The reaction can be carried out in the presence of a catalyst The catalyst can be a base. Preferably, the base is N,N-dimethylamino-pyridine. The basic catalyst is preferably a tertiary amine such N-methyl morpholine, N,N-dimethylaminopyridine, and mixtures thereof. The tertiary amine base is of the formula N(A1)(A2)(A3), contains $C_3$-$C_{15}$ carbon atoms wherein A1, A2, and A3 are each independently selected from a $C_1$-$C_{10}$ alkyl group and a $C_5$-$C_{12}$ aromatic group, wherein A1, A2, and A3 can further include an oxygen or a nitrogen (such as cyclic structures like morpholino and pyridine groups). In one embodiment A1 and A2 are methyl groups, and A3 is a $C_5$-$C_{12}$ aromatic group containing a nitrogen or an oxygen atom (such as cyclic structures like morpholino and pyridine groups).

Prior to the combining step with the compound of formula 3a, the compound of formula 3 can be dissolved in an organic solvent. The organic solvent can be a C1-C4 chlorinated hydrocarbon, such as methylene dichloride. Typically, the compound of formula 3a and the catalyst are mixed with a solution of the compound of formula 3 in an organic solvent, to obtain a reaction mixture. The reaction mixture can be at a temperature of about −20° C. to about −60° C., such as at about −30° C. to about −50° C. The reaction mixture can be maintained for a period of about 10 to about 30 hours, such as about 15 to about 25 hours.

The invention provides a compound of formula 7 having the following structure:

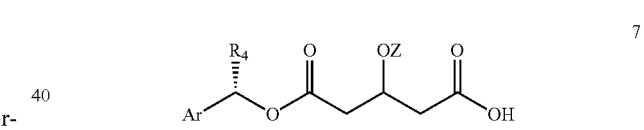

7 wherein $R_4$ is $C_1$-$C_6$ alkyl, e.g., methyl or ethyl, Ar is phenyl or substituted phenyl as defined above, and Z is a hydroxy protecting group as above. Also provided is a compound of formula 7 which is at least 50% chiral pure as determined by chiral HPLC. The compound of formula 7 can be purified by HPLC. The enriched enantiomer of formula 7 has the following structure;

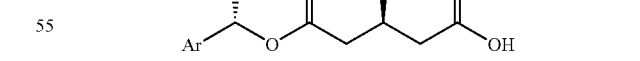

7a

The invention provides a compound of formula 8 having the following structure:

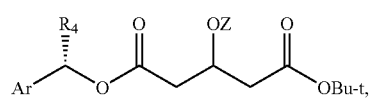

8 wherein Z is a hydroxy protecting group as above, $R_4$ is $C_1$-$C_6$ alkyl, preferably $C_1$-$C_4$ alkyl e.g., methyl or ethyl, and Ar is phenyl or substituted phenyl as defined above. Also provided is a compound of formula 8 which is at least 50% chiral pure as measured by an HPLC chiral column. The compound of formula 8 can be purified by HPLC. The enriched enantiomer of formula 8 has the following structure;

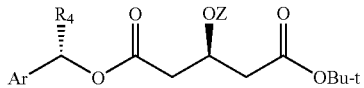

8a

The present invention further provides a process for the preparation of the compound of formula 8, described above, by combining a compound of formula 7, described above, with BOC anhydride. A $C_5$-$C_{12}$ aromatic hydrocarbon such as toluene can be used as a solvent. Preferably, the process is done in the presence of a basic catalyst. The basic catalyst can be selected from the group of tertiary amines consisting of: N-methyl morpholine, N,N-dimethylaminopyridine, and mixtures thereof. The tertiary amine base is of the formula N(A1)(A2)(A3), contains $C_3$-$C_{15}$ carbon atoms wherein A1, A2, and A3 are each independently selected from a $C_1$-$C_{10}$ alkyl group and a $C_5$-$C_{12}$ aromatic group, wherein A1, A2, and A3 can further include an oxygen or a nitrogen (such as cyclic structures like morpholino and pyridine groups). In one embodiment A1 and A2 are methyl groups, and A3 is a $C_5$-$C_{12}$ aromatic group containing a nitrogen or an oxygen atom (such as cyclic structures like morpholino and pyridine groups). Preferably, the combination of the compound of formula 7 with BOC anhydride, is maintained at a temperature of about 5° C. to about 50° C., more preferably at about 10° C. to about 30° C. Preferably, the combination is maintained for a period of about 2 to about 10 hours, more preferably for about 2 to about 5 hours.

The invention provides a process for preparing a compound of formula 6, having the following structure:

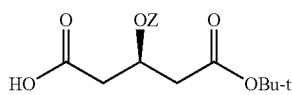

6

The hydrolysis is carried out under basic conditions in an alcohol. The concentration of the alkaline solution can be about 1 to about 2N. The alcohol is can be a C1-C4 alcohol, preferably selected from the group consisting of: methyl alcohol, ethyl alcohol, and mixtures thereof, more preferably ethyl alcohol. Preferably, the combination of the an alkaline solution and the alcoholic mixture of the compound of formula 8, is maintained for a period of about 10 to about 30 hours, more preferably for about 15 to about 25 hours. Preferably, the combination is maintained at a temperature of about 20° C. to about 60° C., more preferably at about 40° C. to about 55° C. Examples of suitable bases include alkali metal and alkaline earth metal bases, particularly hydroxide bases such as sodium and potassium hydroxide. After the hydrolysis, the reaction mixture can be acidified. Compound of 6 can then be extracted into a water immiscible solvent such as toluene, followed by evaporation of the toluene, such as at a pressure of less than one atmosphere.

The invention provides a process for preparing a compound of formula 6, having the following structure:

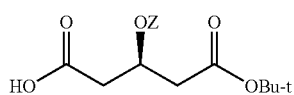

6 by selectively hydrolyzing the compound of formula 8, wherein Z is a hydroxy protecting group as above. The hydrolysis comprises combining an alkaline solution with the alcoholic mixture of the compound of formula 8. Preferably, the concentration of the alkaline solution is about 1 to about 2N. Optionally, the alcohol is selected from the group consisting of: $C_1$-C5 alcohol (preferably $C_1$-$C_4$) such as methyl alcohol, ethyl alcohol, and mixtures thereof.

The present invention provides a process for preparing the compound of formula 4a, having the following structure:

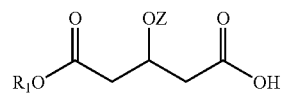

4a by enantioselectively opening the prochiral anhydride compound of formula 3, described above, by combining it with $C_1$-$C_5$ alkyl alcohols (R1-OH) in the presence of alkaloids, wherein Z is a hydroxy protecting group as above.

Preferably, the compound of formula 4a is obtained in the enantiomeric ratio of about 85:15 to about 95:5. Preferably, the compound of formula 4a is combined with an organic solvent. The organic solvent may be $C_6$-$C_{12}$ aromatic hydrocarbon, $C_1$-$C_4$ chlorinated hydrocarbon, $C_4$-$C_8$ ether and or $C_3$-$C_8$ ether. Examples of these solvents include methylene dichloride, toluene, methyl t-butyl ether, n-heptane, methyl ethyl ketone, tetrahydrofuran, and mixtures thereof. The more preferred solvents are methylene dichloride and toluene. Typically, the reaction temperature is about −30° C. to about −60° C., and more preferably, about −40° C. to about −50° C. Typically, the reaction is maintained for about 5 to about 30 hours, more preferably, for about 8 to about 15 hours.

The present invention provides a process for preparing compound of formula 5a, having the following structure:

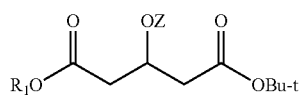

5a by combining the compound of formula 4a, described above with BOC anhydride in the presence of a catalyst (in the form of a base), wherein Z is a hydroxy protecting group as above and $R_1$ is $C_1$-$C_6$ alkyl, preferably C1-C4 group.

The base can be selected from the group consisting of: tertiary amines like N-methyl morpholine, N,N-dimethyl amino pyridine and mixtures thereof. The tertiary amine base is of the formula N(A1)(A2)(A3), contains $C_3$-$C_{15}$ carbon atoms wherein A1, A2, and A3 are each independently selected from a $C_1$-$C_{10}$ alkyl group and a $C_5$-$C_{12}$ aromatic group, wherein A1, A2, and A3 can further include an oxygen or a nitrogen (such as cyclic structures like morpholino and pyridine groups). In one embodiment A1 and A2 are methyl groups, and A3 is a $C_5$-$C_{12}$ aromatic group containing a nitrogen or an oxygen atom (such as cyclic structures like morpholino and pyridine groups). Preferably, the temperature is of about −10° C. to about 50° C., more preferably about 10° C. to 30° C. Preferably, the combination of the compound of formula 4a, BOC anhydride and the base is maintained for about 2 to 10 hours, more preferably for 2 to about 5 hours.

The present invention provides a process for preparing compound of formula 6a, having the following structure:

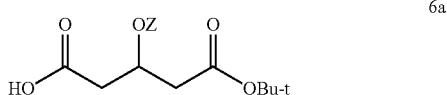

6a by selectively hydrolyzing the compound of formula 5a, described above, wherein Z is a hydroxy protecting group.

Preferably, the compound of formula 6a is obtained in the enantiomeric ratio of about 85:15 to about 95:5.

The hydrolysis comprises adding about 0.5 to about 2N alkaline solution to the alcoholic mixture of the compound of formula 5a. The alcohol may be selected from the group consisting of: methyl, ethyl alcohol, and mixtures thereof. The hydrolyzation is for about 2 to about 12 hours at a temperature of about 20° C. to about 60° C., more preferably for about 6 to about 8 hours at a temperature of about 45-55° C. The base can be selected from the group consisting of: tertiary amines like N-methyl morpholine, N,N-dimethyl amino pyridine and mixtures thereof. The tertiary amine base is of the formula $N(A1)(A2)(A3)$, contains $C_3$-$C_{15}$ carbon atoms wherein A1, A2, and A3 are each independently selected from a $C_1$-$C_{10}$ alkyl group and a $C_5$-$C_{12}$ aromatic group, wherein A1, A2, and A3 can further include an oxygen or a nitrogen (such as cyclic structures like morpholino and pyridine groups). In one embodiment A1 and A2 are methyl groups, and A3 is a $C_5$-$C_{12}$ aromatic group containing a nitrogen or an oxygen atom (such as cyclic structures like morpholino and pyridine groups).

The present invention provides a compound of formula 7 having the following structure:

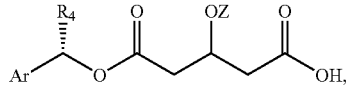

7 wherein $R_4$ is $C_1$-$C_6$ alkyl, e.g., methyl or ethyl, Ar is phenyl or substituted phenyl as defined above, and Z is a hydroxy protecting group as above.

The present invention also provides a process for preparing the compound of formula 7a by enantioselectively opening the prochiral anhydride of formula 3, described above with chiral alcohols of the formula 3a, described above.

Preferably, the compound of formula 7a is in the enantiomeric ratio of about 80:20 to about 85:15.

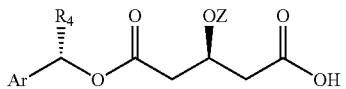

7a

The reaction comprises combining a solution of a compound of formula 3a with a mixture of a compound of formula 3 and a base in an organic solvent. Preferably, the temperature during the process is of about −20° C. to about −60° C. and more preferably, of about −30° C. to about −50° C. Preferably, combination of the compound of formula 3a, the compound of formula 3, the base and the organic solvent, is maintained for about 10 to about 30 hours, more preferably for about 15 to about 25 hours. The base can be selected from the group consisting of: tertiary amines like N-methyl morpholine, N,N-dimethyl amino pyridine and mixtures thereof. The tertiary amine base is of the formula $N(A1)(A2)(A3)$, contains $C_3$-$C_{15}$ carbon atoms wherein A1, A2, and A3 are each independently selected from a $C_1$-$C_{10}$ alkyl group and a $C_5$-$C_{12}$ aromatic group, wherein A1, A2, and A3 can further include an oxygen or a nitrogen (such as cyclic structures like morpholino and pyridine groups). In one embodiment A1 and A2 are methyl groups, and A3 is a $C_5$-$C_{12}$ aromatic group containing a nitrogen or an oxygen atom (such as cyclic structures like morpholino and pyridine groups). Preferably, the organic solvent is a $C_6$-$C_{12}$ aromatic hydrocarbon or $C_1$-$C_4$ chlorinated hydrocarbon. Specific examples of these solvents include methylene dichloride, toluene and mixtures thereof.

The present invention provides a compound of formula 8 having the following structure:

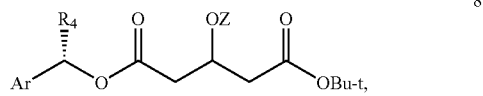

8 wherein Z is a hydroxy protecting group as above and $R_4$ is $C_1$-$C_6$ alkyl, or a $C_1$ to $C_6$ carbon The enantiomeric enriched form of formula 8 has the following structure;

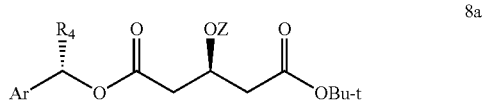

8a

The present invention also provides a process for preparing the compound of formula 8a by combining the compound of formula 7a, described above, with BOC anhydride in the presence of a base, wherein Z is a hydroxy protecting group as above and $R_4$ is alkyl of $C_1$ to $C_6$ carbon group, preferably C1-C4 group.

The base can be selected from the group consisting of: tertiary amines like N-methyl morpholine, N,N-dimethyl amino pyridine and mixtures thereof. The tertiary amine base is of the formula $N(A1)(A2)(A3)$, contains $C_3$-$C_{15}$ carbon atoms wherein A1, A2, and A3 are each independently selected from a $C_1$-$C_{10}$ alkyl group and a $C_5$-$C_{12}$ aromatic group, wherein A1, A2, and A3 can further include an oxygen or a nitrogen (such as cyclic structures like morpholino and pyridine groups). In one embodiment A1 and A2 are methyl groups, and A3 is a $C_5$-$C_{12}$ aromatic group containing a nitrogen or an oxygen atom (such as cyclic structures like morpholino and pyridine groups). Preferably, the temperature during the process is of about −10° C. to about 50° C., more preferably about 10° C. to 30° C. Preferably, the combination of the compound of formula 7a with BOC anhydride in the presence of a base is maintained for about 2 to about 10 hours, more preferably for about 2 to about 5 hours.

The present invention also provides a process for preparing compound of formula 6a having the following structure:

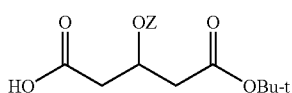

6a by selectively hydrolyzing the compound of formula 8a, described above, wherein Z is a hydroxy protecting group as above.

Preferably, the compound of formula 6a is obtained in an enantiomeric ratio of about 80:20 to about 85:15. The enantiomeric enriched formula 6 has the following structure;

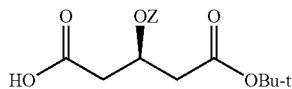

6

The hydrolysis comprises combining about 0.5 to about 2N alkaline solution with an alcoholic mixture of the compound of formula 8a. The alcohol may be selected from the group consisting of: $C_1$-$C_4$ alcohol such as methanol, ethanol and mixtures thereof. The combination of the alkaline solution and the an alcoholic mixture of the compound of formula 8a is preferably maintained for about 10 to about 30 hours, preferably at a temperature of about 20° C. to about 60° C., more preferably for a period of about 15 to about 25 hours at a temperature of about 40° C. to about 55° C.

The compound of formula 6 may be used to prepare the compound of formula 2, having the following structure:

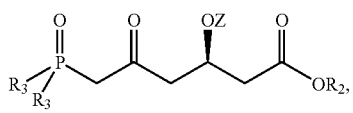

2 wherein $R_2$ is a $C_1$-$C_4$ alcohol such as methyl, ethyl, or t-butyl; Z is a hydroxy protecting group; and $R_3$ is $C_1$ to $C_3$ alkoxy, aryloxy, or substituted aryloxy group. The protecting group is preferably a silyl group, including trialkylsilysl group having the formula-Si(A)$_3$ where each A is independently selected from a C1-C6 linear or branched aliphatic or aromatic group. Examples of silyl groups include trimethylsilyl, triethylsilyl, triisopropylsilyl, tert-butyldiphenylsilyl, tert-butyldimethylsilyl, methyldiphenylsilyl, and dimethylphenylsilyl.

The present invention also provides a process for preparing the chiral pure R-isomer compound of formula 6, described above, by an optical resolution process by combining the compound of formula 6a, described above, a compound (R)-(+)-phenylethylamine of formula 9a, having the following structure:

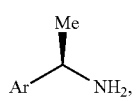

9a or a compound (S)-(−)-phenylethylamine of formula 9b, having the following structure:

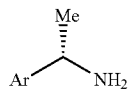

9b

The resolution comprises combining the compound of formula 6a with chiral ratio of about 80:20 to about 85:15 with compound of formula 9a or 9b to get a salt of formula 8b, having the following structure:

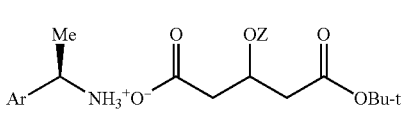

8b in an aliphatic alcoholic solvent is a $C_1$-$C_4$ alcohol selected from the group consisting of: as methanol, ethanol, isopropyl alcohol, n-butyl alcohol and t-butyl alcohol, more preferably isopropyl alcohol. The compound of formula 9a is used in a molar ratio of about 1 to about 2 to the compound of formula 6a at a temperature of about 0° C. to about 70° C. The obtained product is crystallized to get chirally pure salt of formula 8c having the following structure:

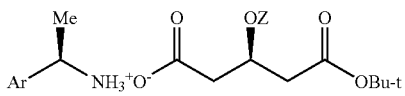

8c

The salt of formula 8c is hydrolyzed in aqueous medium using a mineral acid to get the compound of formula 6 with chiral purity of about 99 to about 100%, more preferably about 99.5 to about 99.8%. The mineral acid may be: a dilute hydrochloric acid or dilute sulfuric acid. Preferably dilute hydrochloric acid is used. Hydrochloric acid is added in an amount of about 1 to about 2 equivalents with regard to the compound of formula 8c, at a temperature of about 0° C. to about 50° C., preferably at about 0° C. to about 30° C.

The present invention provides a compound of formula 9, having the following structure:

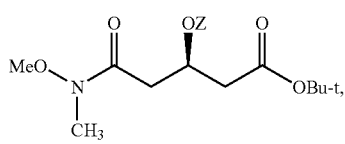

9 wherein Z is a hydroxy protecting group.

The compound of formula 9 may be used to prepare the compound of formula 2, having the following structure:

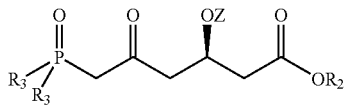

by reaction of compound 9 with a metal salt of dialkyl alkylphosphonate of the general formula:

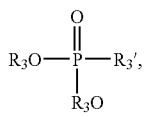

wherein Z is a hydroxy protecting group, as described above; $R_2$, and $R_3$ are, independently, an optionally substituted alkyl of 1-4 carbon atoms; X is an alkoxy group of $C_1$ to $C_5$ carbon atoms or an optionally substituted alkyl group of $C_1$-$C_5$ carbons. Preferably all $R_3$ groups (including $R_3$ prime) are methyl groups. To form the Wittig reagent (ylide), the phosphonium salt depicted above is suspended in a solvent such as diethyl ether or THF (tetrahydrofuran) and a strong base, preferably a $C_1$-$C_8$ aryl or alkyl metal base, such as the organolithium reagents phenyllithium or n-butyllithium is added. The lithium salt has the following structure:

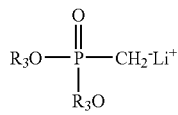

Preferably, a $C_1$-$C_4$ dialkyl phosphonate is used, and more preferably dimethyl methylphosphonate is used in the process of the invention.

Preferably, the solvent is selected from $C_1$-$C_4$ aliphatic alcoholic solvent, a $C_6$-$C_{10}$ aromatic and $C_5$-$C_8$ aliphatic hydrocarbon, a $C_2$-$C_8$ aliphatic ester, a $C_4$-$C_8$ ether (including cyclic compounds), and a C1-C6 aliphatic solvent with one, two or three chlorine atoms.

Examples of such solvents include toluene, benzene, xylene, cyclohexane; ethers, methyl t-butyl ether, tetrahydrofuran and tetrahydrofuran. Preferably the solvent is tetrahydrofuran. Suitable bases include alkyl lithium bases, such as n-butyl lithium and $C_1$-$C_8$ alkyl metals, preferably in the amount of 1-5 equivalents based on the compound of formula (XII), more preferably in the amount of 3-4 equivalents.

As exemplified, a compound of formula:

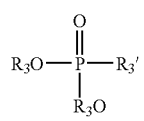

as described above, preferably dimethylmethylphosphonate is combined with a suitable solvent such as a $C_4$-$C_8$ ether such as tetrahydrofuran. The reaction mixture is then cooled before addition of a strong base such an organolithium reagent such as phenyllithium or n-butyllithium. The reaction is maintained to obtain anion formation. Compound of formula 9 is then added to the reaction mixture, preferably in the same solvent. The reaction mixture is obtained to complete the reaction. The reaction can be quenched by addition of ammonium chloride. The reaction can be carried out at a preferred temperature of about −70° C. to about −90° C. Afterwards, the reaction mixture can be warmed, such as to about 25° C. The product, compound of formula one can be extracted into a water immiscible solvent such as hexane. The hexane can then be evaporated to obtain the product.

The present invention also provides a process for preparing the compound of formula 9, by combining the compound of formula 6, described above, with at least one organic solvent selected from the group consisting of: $C_5$-$C_{12}$ aromatic hydrocarbons (including substituted), $C_6$-$C_{10}$ aliphatic hydrocarbons, halogenated $C_6$-$C_{10}$ hydrocarbons, ethers having from 2 to 20 carbon atoms and ketones having from 2 to 20 carbon atoms, an amidation reagent selected from the group consisting of: $C_{1-4}$ alkyl and $C_{6-8}$ aryl haloformates and acid halides, and at least one base; and adding N,O-dimethyl hydroxylamine.

Preferably, the $C_{1-4}$ alkyl haloformate is ethyl or methyl derivative of chloro or bromo formate. Preferably, the $C_{6-8}$ aryl haloformate is a benzyl chloro or bromo formate. Preferred acid halides are acetyl, pivaloyl, oxaloyl or benzoyl chlorides and bromides. The most preferred haloformate is either ethyl chloroformate or methyl chloroformate. The more preferred acid halide is acetyl or pivaloyl chlorides.

Preferably the substituted aromatic hydrocarbon is either toluene or xylene. A preferred $C_6$-$C_{10}$ aliphatic hydrocarbon is either hexane or heptane. Preferred ketones are acetone, methyl ethyl ketone or methyl isobutyl ketone. Preferably the ethers are diethyl ether, diisopropyl ether or t-butyl methyl ether. Preferably the halogenated hydrocarbon is methylene dichloride. The more preferred organic solvent is either acetone or methylene dichloride.

Preferably the base is an organic base selected from the group consisting of: diethyl amine, triethyl amine, di-n-propyl amine, diisopropyl amine, tri-n-butyl amine, morpholine, piperidine, pyridine, N,N-dimethyl aminopyridine. Preferably, the base is either N,N-dimethylaminopyridine or triethyl amine.

Preferably, the compound of formula 6 and an organic solvent first combined, and thereafter are combined with the amidation reagent and a base at a temperature of about 20° C. to about −30° C., more preferably of about −10° C. to about −20° C., to obtain a reaction mixture. Preferably, prior to the addition of the solution of N,O-dimethyl hydroxylamine, the reaction mixture is maintained at a temperature of about −10 to −20° C. for a period of about 0 to about 4 hours. Preferably the reaction mixture is maintained for about 0.5 to about 2 hours after the addition of N,O-dimethyl hydroxylamine at a temperature of about −10° C. to about 35° C., more preferably at about 0° C. to about 20° C.

The invention provides a process for the preparation of a chirally pure compound of the general formula A, having the following structure:

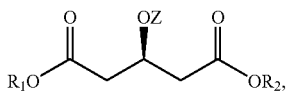

A wherein $R_1$ is H, $C_1$-$C_5$ alkyl; $R_2$ is $C_1$-$C_6$ alkyl, e.g., methyl, ethyl, or t-butyl group; and Z is a hydroxy protecting group, optionally a trimethylsilyl, t-butyldimethylsilyl, diphenylmethylsilyl, or dimethyl phenylsilyl group. Preferably the silyl group is tert-butyldimethylsilyl. Preferably, $R_2$ is t-butyl group.

The compound of formula A is an intermediate used for the synthesis of the compound of formula 2, having the following structure:

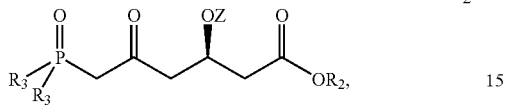

wherein $R_2$ is methyl, ethyl, or t-butyl group; Z is hydroxy protecting group such as trimethylsilyl, t-butyldimethylsilyl, diphenylmethylsilyl, or dimethyl phenylsilyl group, and $R_3$ is $C_1$ to $C_3$ alkyloxy, aryloxy, or substituted aryloxy group, which can be used for the preparation of HMG-CoA reductase inhibitors.

The present invention provides a process for preparing a compound of formula 2a, having the following structure:

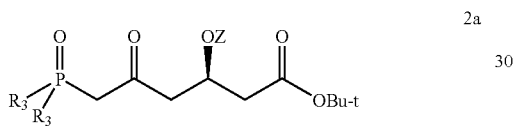

by combining the compound of formula 9, described above with a lithiated salt of dialkyl phosphonate, wherein $R_3$ is lower $C_1$ to $C_3$ alkyloxy, $C_5$-$C_{12}$ aryloxy, $C_5$-$C_{12}$ aryloxy (optionally substituted) and Z is a hydroxy protecting group, such as trimethylsilyl, t-butyldimethylsilyl, or diphenyl methylsilyl, dimethylphenylsilyl.

Preferably, the dialkyl phosphonate is $C_1$-$C_3$ dialkyl phosphonate. The lithiated salt of dialkyl phosphonate is prepared at a temperature of about –50° C. to about –110° C. using n-butyl lithium and dialkyl phosphonate in the molar ratios of about 1.3 to about 4.5 and about 1.5 to about 5, respectively, in relation to compound of formula 9. More preferably, the molar ratios are about 1.4 to about 2 and about 1.5 to about 2.2, respectively. The reaction is maintained preferably at a temperature of about –75° C. to about –85° C. for about 2 to about 6 hours. After the addition of solution of compound of formula 9, the reaction is maintained preferably at a temperature of about –75° C. to about –85° C. for about 0 to about 4 hours.

The reaction is done preferably using toluene, xylene, cyclohexane, methyl t-butyl ether, tetrahydrofuran, or mixtures thereof. More preferably the solvent is selected from methyl t-butyl ether and tetrahydrofuran.

In any of the embodiments of the above process, and compounds, the group $R_1$ is preferably $C_1$-$C_4$ group, more preferably methyl; $R_2$ is preferably a $C_1$-$C_4$ group, more preferably t-butyl; Z is preferably a silyl group, more preferably tert-butyldimethylsilyl.

The compounds prepared by the process of the invention may be used to prepare statins for treatment of hyperlipidemia. Statins can be combined with a pharmaceutically acceptable excipient to prepare pharmaceutical compositions.

The statins that can be prepared include the following

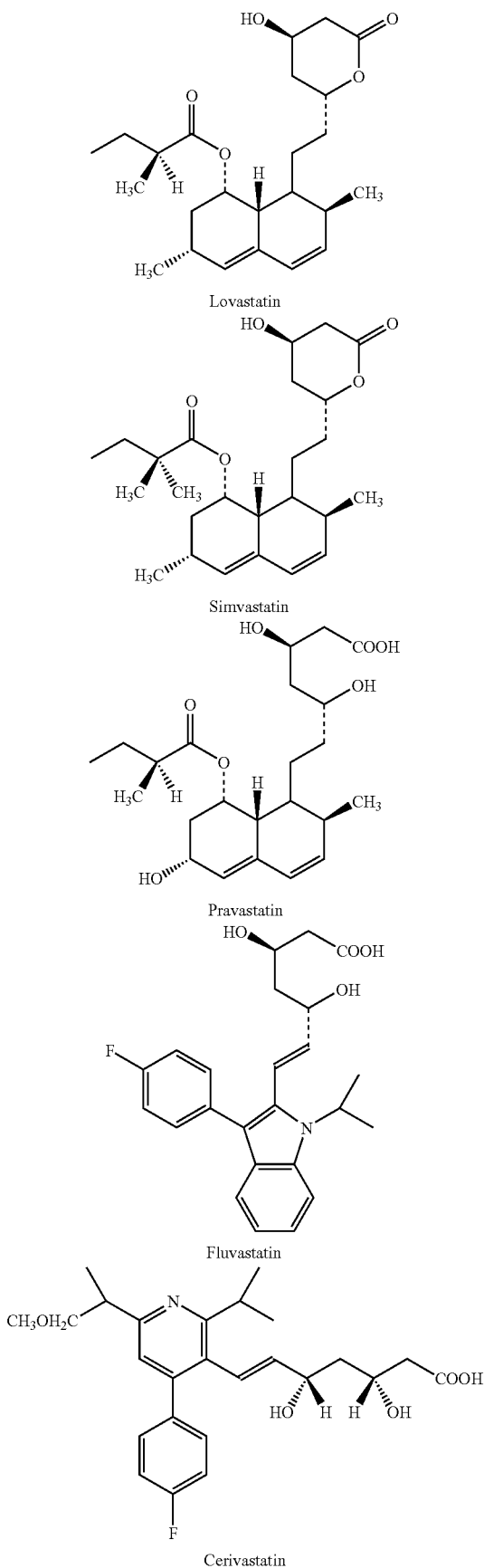

-continued

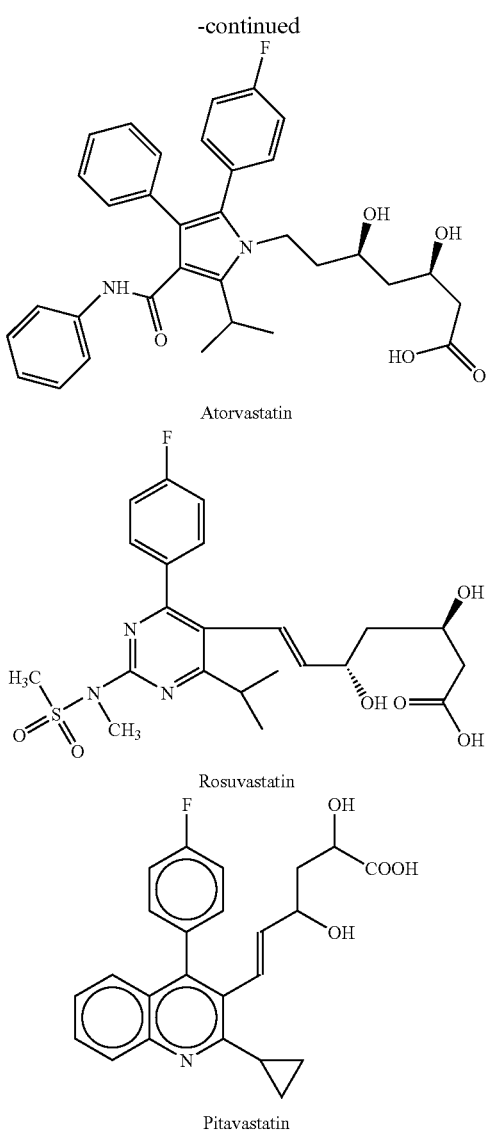

Atorvastatin

Rosuvastatin

Pitavastatin

For example, Helvetica Chemica Acta, vol. 90 (2007), which is incorporated herein by reference, discloses a pitavastatin aldehyde precursor having the structure:

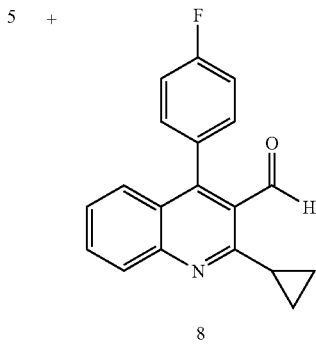

WO2007/041666 and WO2006/091771, incorporated herein by reference, further disclose preparation of rosuvastatin through the Wittig reaction. After the Wittig reaction, the protecting group (Z) is removed, followed by reduction to obtain a diol, followed by hydrolysis of the ester to obtain a pharmaceutically acceptable salt.

NMR Data for Compound VII:
0.07 (d, 3H); 0.76 (d, 3H); 1.47 (d, 3H); 2.5 (q, 4H); 4.87 (p, 1H); 5.82 (q, 1H); 7.29 (m, 5H)

NMR Data for Compound IX:
0.10 (s, 6H); 0.87 (s, 9H); 2.63-2.44 (m, 3H); 2.848 (q, 1H), 3.18 (s, 2H); 3.71 (s, 2H); 4.23 (q, 2H), 4.59 (q, 1H)

for Rosuvastatin Ca
BUFFER:—0.05% v/v Acetic acid glasial pH 3.5 with 5% Ammonium hydroxide.
ELUENT (A):—Mix. 60% buffer 35% acetonitrile 5% ethanol.
ELUENT (B):—55% buffer 45% ethanol.
ELUENT (C):—ETHANOL.
COLUMN:—Discovery HS C18,3 µm (150×4.6) mm
FLOW:—0.5 ml/min, INJ. VOL.: –10 µl, WAVELENGTH: –243 nm.
COLUMN TEMP.:—20° C., AUTOSAMPLER TEMP.: –4° C.
RUN TIME:—25.0 MIN, EQUILIBRATION TIME: –7.0 MIN
GRADIENT:—

| | Gradient: | | | | | |
|---|---|---|---|---|---|---|
| TIME | FLOW | % A | % B | % C | % D | CURVE |
| 0.00 | 0.5 | 100 | 0 | 0 | 0 | 6 |
| 15.00 | 0.5 | 0 | 100 | 0 | 0 | 6 |
| 20.00 | 0.5 | 0 | 93 | 7 | 0 | 6 |
| 25.00 | 0.5 | 0 | 64 | 36 | 0 | 6 |
| 25.10 | 0.5 | 100 | 0 | 0 | 0 | 6 |

Instrument
Gas Chromatograph equipped with Flame Ionisation Detector.

Column
DB 17, 30 m×0.53 mm×1.0 µm film thickness, Agilent C/N: 125-1732 or equivalent.

Chromatographic Conditions

| | | |
|---|---|---|
| a.) | Initial oven temperature | 40° C. |
| b.) | Initial hold time | 3.0 minute |
| c.) | Initial-1 ramp rate | 20° C./minute |
| d.) | Intermediate-1 oven temperature | 160° C. |
| e.) | Intermediate-1 hold time | 10.0 minute |
| f.) | Initial-2 ramp rate | 10° C./minute |
| g.) | Intermediate-2 oven temperature | 210° C. |
| h.) | Intermediate-2 hold time | 10.0 minute |
| i.) | Final ramp rate | 20° C./minute |
| j.) | Final oven temperature | 270° C. |
| k.) | Final hold time | 10.0 minute |
| l.) | Injector temperature | 180° C. |
| m.) | Detector temperature | 300° C. |
| n.) | Carrier gas (He) flow | 10.0 ml/min |
| o.) | Mode | Constant flow |
| p.) | Injection volume | 1.0 µl |
| q.) | Split ratio | Splitless |

Temperature and flow rate may be varied in order to achieve the required system suitability.

Diluent

Acetonitrile

Preparation of System Suitability Solution

Weighed accurately about 20 mg of each: TBDMS-OH, DMMP, MBSG and 19TBPO into 10 ml volumetric flask, dissolve and brought to volume with diluent. Transferred 1 ml of the stock solution into 10 ml volumetric flask and brought to volume with diluent.

System Suitability Test

Injected System Suitability Solution.

Typical retention times are about 4 minutes for TNDMS-OH peak, about 6.5 minutes for the DMMP peak, About 14.5 minutes for the MBSG peak and 31.5 minutes for the 19TBPO peak.

Preparation of Sample Solution

Weighed accurately 20 mg of sample into 10 ml volumetric flask, dissolved and brought to volume with diluent.

EXAMPLES

General Preparation of 3-hydroxy Protected Glutaric Acid

A four-neck round bottom flask fitted with a mechanical stirrer, condenser and charging tube, was charged with methylene dichloride (675 ml) followed by charging of imidazole (187.2 g), t-butyldimethylsilyl chloride (248.3 g) under nitrogen atmosphere. Reaction mass was maintained for 1-2 hours at 20-30° C. followed by addition of a solution of 3-hydroxy diethyl glutarate in methylene chloride (225 g). The mass was maintained for 4-6 hours followed by water and brine washing of the reaction mass. Methylene dichloride under vacuum at 30-35° C. was distilled out and residue was charged into a solution of 30-40% aq. methyl alcohol (1850 ml), sodium hydroxide (96.8 g) at 25-35° C. and mixed for 20-30 hours. Solvent is distilled out under vacuum at 40-45° C., mass was further diluted with water and 1-12N hydrochloric acid was added to bring pH to 2.5-4 and the product was extracted with t-butyl methyl ether and concentrated to give 71% of 3-hydroxy protected glutaric acid.

Example 1

Preparation of 3-hydroxy Protected Glutaric Anhydride, Compound of Formula 3

A four-neck round bottom flask fitted with a mechanical stirrer, condenser, and charging tube was charged with acetic anhydride (609 ml) followed by charging of 3-hydroxy protected glutaric acid at 25 to 30° C. The reaction mass was refluxed for 2-3 hours at 130-135° C. The unreacted acetic anhydride, along with acetic acid, was completely distilled under vacuum at 60-95° C. The product was crystallized from cyclohexane, and dried to obtain 90-95% of a brown crystalline solid with GC purity of 97.2%.

Example 2

Preparation of 3-(t-butyldimethylsilanyloxy)-1,5-pentane dioic Acid Monomethyl Ester, Compound of Formula 4

A four neck round bottom flask fitted with a mechanical stirrer, condenser, and charging tube was charged with methylene dichloride (75 ml) and the compound of formula 3 (25 g, 0.1 mole) under inert atmosphere at 25 to 30° C. The reaction mass was cooled to −35 to −40° C., followed by addition of a solution of quinidine (35.68 g, 0.11 mole) in methylene dichloride (125 ml). The methanol (28.3 ml) was slowly added into the reaction mass at −35 to −40° C. and it was maintained for 15-20 hours. Methylene dichloride was distilled off under vacuum, at 25-35° C., followed by addition of sufficient amount of methyl t-butyl ether and water (25 ml). The pH of the reaction mass was adjusted to 4-5 using hydrochloric acid. The aqueous phase was separated. The organic phase was washed with acidic water to remove quinidine, followed by removal of methyl t-butyl ether under vacuum, to give the compound of formula 4 in 96% yield, with chiral purity of 93:7 and GC purity of 99.25%.

Example 3

Preparation of 3-(t-butyldimethylsilanyloxy)-1,5-pentane dioic Acid monomethyl ester, Compound of Formula 4

A four neck round bottom flask fitted with a mechanical stirrer, condenser and charging tube, was charged with toluene (500 ml), followed by charging of the compound of formula 3 (50 g, 0.181 mole) under inert atmosphere at 25 to 30° C. The reaction mass was cooled to −30 to −55° C., followed by addition of quinidine (76.33 g, 0.235 mole). The methanol (55 ml) was slowly added into the reaction mass at −30 to −55° C. and it was maintained for 10-20 hours. Water (25 ml) was added and the pH was adjusted to 4-5 using hydrochloric acid. The aqueous phase was separated. The organic phase was washed with acidic water to remove quinidine, followed by removal of toluene under vacuum, giving the compound of formula 4a in 83.5% yields, with chiral purity of 93.2: 6.8 and GC purity of 96.6%.

Example 4

Preparation of Compound of Formula 5

A four neck round bottom flask fitted with a mechanical stirrer, condenser and charging tube, was charged with methylene dichloride (40 ml), followed by charging of the compound of formula 4 (10 g, 0.036 mole) at −5 to 0° C. N-methyl morpholine (4.3 g, 0.043 mole) was added to the reaction mass at −5 to 0° C. and the reaction was maintained for 15-30 minutes, followed by slow addition of BOC anhydride (111.8 g, 0.055 mole) in methylene dichloride (40 ml) at −5 to 0° C. The reaction was maintained for 15-30 minutes. A catalytic amount of N,N-dimethylaminopyridine was added at −5 to 0° C., and the mass was maintained at 25-30° C. for 3-5 hours. Silica gel (2.5 g) was added, followed by removal of silica gel. Water (30 ml) was added to the reaction mass and the pH was adjusted to 4-4.5 using hydrochloric acid. The aqueous phase was separated and the organic phase was washed with water, followed by removal of methylene dichloride under vacuum, giving the compound of formula 5 in 97.6% yield with GC purity of 92.9%

Example 5

Preparation of Compound of Formula 6

A four neck round bottom flask fitted with a mechanical stirrer, condenser and charging tube, was charged with ethanol (50 ml), followed by charging with the compound of formula 5 (10 g, 0.03 mole) at 20 to 30° C. 1-2N Sodium hydroxide solution (40 ml) was added into the reaction mass at 45 to 50° C. and it was maintained for 5-8 hours, followed by removal of ethanol under vacuum. Water (50 ml) was added to the reaction mass and the pH was adjusted to 5-6 using hydrochloric acid. Toluene (25 ml) was added and the aq. phase was separated, followed by removal of toluene under vacuum to give the compound of formula 6 in 93% yield.

Example 6

Preparation of Compound of Formula 7

A four neck round bottom flask fitted with a mechanical stirrer, condenser and charging tube, was charged with methylene dichloride (50 ml) followed by charging with the compound of formula 3 (10 g, 0.041 mole) under inert atmosphere at 25 to 30° C. The mass was cooled to −30 to 35° C. followed by addition of the compound of formula 3a (7.5 g, 0.0615 mole). N,N-Dimethylaminopyridine (7.5 g, 0.0615 mole) in methylene dichloride (30 ml) was slowly added into the reaction mass at −30 to −35° C. and it was maintained for 15-20 hours. Water (50 ml) was added to the reaction mass and the pH was adjusted to 4-5 using hydrochloric acid. The aqueous phase was separated, and the organic phase was washed with water, followed by removal of methylene dichloride under vacuum, giving the compound of formula 7 in 96% yield with chiral purity of 80.5:19.5.

Example 7

Preparation of Compound of Formula 8

A four neck round bottom flask fitted with a mechanical stirrer, condenser and charging tube, was charged with toluene (6 ml) followed by charging with the compound of formula 7 (1 g, 0.0027 mole) at 20 to 30° C. N-methyl morpholine (0.327 g, 0.034 mole) was added to the reaction mass at 20 to 30° C. and it was maintained for 15-30 minutes. BOC anhydride (0.884 g, 0.004 mole) in toluene (3 ml) was slowly added to the reaction mass and it was maintained for 15-30 minutes. A catalytic amount of N,N-dimethylaminopyridine was added at 20 to 30° C., and the mass was maintained at 25-30° C. for 3-5 hours. Silica gel (2.5 g) was added and then removed. Water (10 ml) was added to the mass, and the pH was adjusted to 4-4.5 using hydrochloric acid. The aqueous phase was separated. The organic phase was washed with water, followed by removal of toluene under vacuum, giving the compound of formula 8 in 62% yield.

Example 8

Preparation of Compound of Formula 6a

A four neck round bottom flask fitted with a mechanical stirrer, condenser and charging tube, was charged with methanol (8 ml), followed by charging with the compound of formula 8 (1 g, 0.0024 mole) at 20 to 30° C. 1-2N Sodium hydroxide solution (8 ml) was added into the reaction mass at 45 to 50° C. and it was maintained for 5-8 hours. Methanol was removed under vacuum at 45 to 50° C. Water (15 ml) was added to the mass and the pH was adjusted to 4-4.5 using hydrochloric acid. Toluene (15 ml) was added and the aqueous phase was separated, followed by removal of toluene under vacuum, giving the compound of formula 6 in 46% yield.

Example 9

Preparation of Compound of Formula 6

A four neck round bottom flask fitted with a mechanical stirrer, condenser and charging tube, was charged with isopropyl alcohol (50 ml), followed by charging with the compound of formula 6a (10 g, 0.031 mole) at 20 to 30° C. (R)-(+)-phenylethyl amine (4.18 g, 0.034 mole) was added over a period of 1-2 hours followed by heating the mass to get a clear solution. Mass was mixed for 2-4 hours at 15-25° C., filtered, and the solid mass was dissolved into water (110 ml). Sodium chloride (33 g) was added to the mass followed by addition of 1.3 mole equivalent of 10% hydrochloric acid. Reaction mass was mixed for 2-4 hours and extracted with sufficient volume of methylene dichloride followed by stripping of methylene dichloride under vacuum to get 76% of the compound of formula 6 with chiral purity of 99.5%

Example 10

Preparation of Compound of Formula 9

A four neck round bottom flask fitted with a mechanical stirrer, condenser and charging tube, was charged with methylene dichloride (210 ml), followed by charging with the compound of formula 6 (35 g, 0.11 mole) at 20 to 30° C. The reaction mass was cooled to −15 to −25° C. followed by addition of triethyl amine (13.34 g) and ethyl chloroformate (13.13 g) and it was maintained for 30-60 minutes at 0 to −15° C. followed by addition of a solution of N,O-dimethyl hydroxylamine (13.95 g) in methylene dichloride (30 ml). Reaction mass was maintained for 1-3 hours at 20-30° C. followed by washing the mass with sufficient quantity of dilute hydrochloric acid, saturated sodium bicarbonate and brine. Stripping of methylene dichloride resulted into 95% yield of compound of formula 9 with GC purity of 95.4%

Example 11

Preparation of Compound of Formula 2

A four neck round bottom flask fitted with a mechanical stirrer, condenser and charging tube, was charged with tetrahydrofuran (25 ml), followed by charging with dimethyl methyl phosphonate (4.3 g, 0.035 mole) at 20 to 30° C. The reaction mass was cooled to −80 to −90° C. followed by addition of 1.6 M n-butyl lithium solution in hexane (2.08 g, 0.033 mole). The reaction mass was maintained for 2-4 hours at −80 to −90° C. followed by addition of a solution of compound of formula 9 (5 g, 0.014 mole) in tetrahydrofuran (5 ml). Reaction mass was maintained for 1-3 hours at −75 to −90° C. followed by quenching of the mass with ammonium chloride solution. The temperature of the reaction mixture was allowed to 20-30° C. Phases were separated and aq. layer was extracted with hexane. Combined organic phase was washed with brine followed by stripping of hexane to get 85% yield of compound of formula 2 with GC purity of 87.1%.

(Examples 12-16 are copied form WO2006/091771)

Example 12

Preparation of Compound 20TB by Wittig reaction from 19TBPH

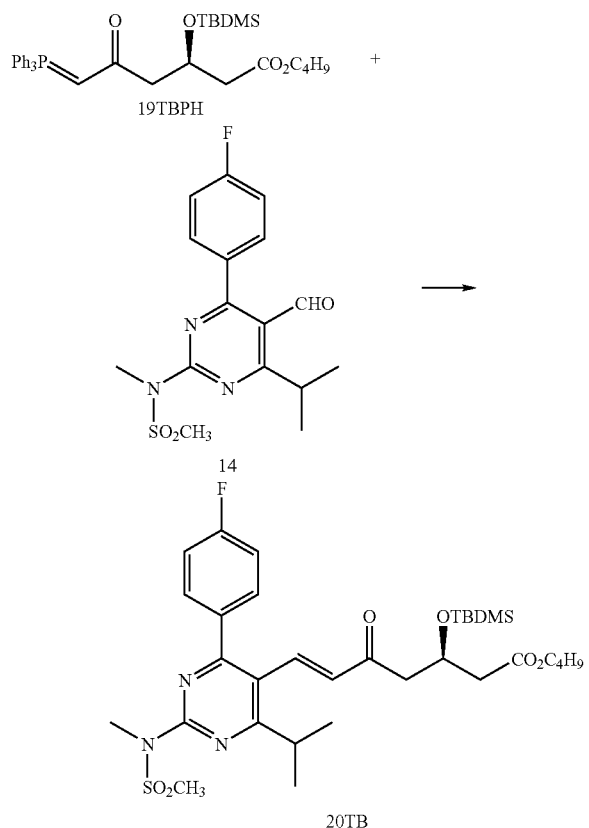

A 100 ml flask, protected from light and provided with $N_2$ flow was charged with Compound 14 (3.6 g, 10.5 mmol), Compound 19TBPH (9.05 g, 15.7 mmol), and dry toluene (36 ml, 10 vol relative to Compound 14). The reaction mixture was heated to about 100° C. for 19.5 hrs. A sample of the reaction mixture was analyzed by HPLC, and contained 1.7% of Compound 14.

Anhydrous $MgCl_2$ (2 g, 2 equivalents relative to Compound 19TBPH) was added to the reaction mixture and the reaction mixture was stirred at 100° C. for 2 hrs. The reaction mixture was cooled to 0° C. for 2 hours, and filtered without washing the solid. A filtrate was obtained and was washed twice with $H_2O$ (100 ml each) and the solvent was evaporated, yielding 7.56 g of a brown solid.

Example 13

Preparation of Compound 20M by Wittig Reaction

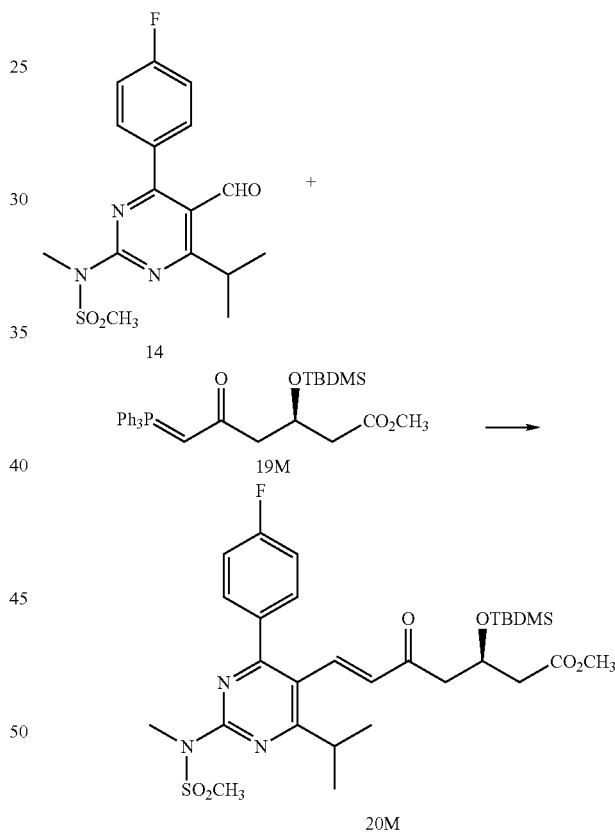

A 250 ml flask, protected from light and provided with $N_2$ flow was charged with Compound 14 (4.38 g, 12.5 mmol), Compound 19M (10 g, 18.7 mmol), and extra dry toluene (100 ml). The reaction mixture was heated to about 100° C. for 15 hrs. After the completion of the reaction, anhydrous $MgCl_2$ (4.8 g, 2.7 eq.) was added to the reaction mixture and the reaction mixture was heated for 2 hours at about 100° C. The reaction mixture was cooled to 0° C. over a period of about 2 hours, filtered, and washed with 45 ml of toluene, yielding 12.73 g of a viscous oil.

Example 14

Preparation of Compound 21TB in HCl/THF

A mixture of HCl (32% in water, 0.57 g), water (2 mL), and THF (17.5 mL) was prepared. 5.4 mL of this mixture were added dropwise to a solution of Compound 20TB (2.7 g) in THF (8.1 mL). The reaction mixture was stirred at ambient temperature overnight, until monitoring of the reaction by TLC indicated completion of the reaction.

Ethyl acetate (20 mL) was added to the reaction mixture and the reaction mixture was washed with water (20 mL). An aqueous layer formed, and was extracted with ethyl acetate (20 mL). The organic layers were combined and washed with an aqueous solution of $Et_3N$ (2×5 mL) at a pH of about 10.5. The organic layer was dried over $MgSO_4$ and the solvent was removed under reduced pressure, yielding an oil of Compound 21TB (2.03 g).

Example 15

Preparation of Compound 22TB (TBRE)

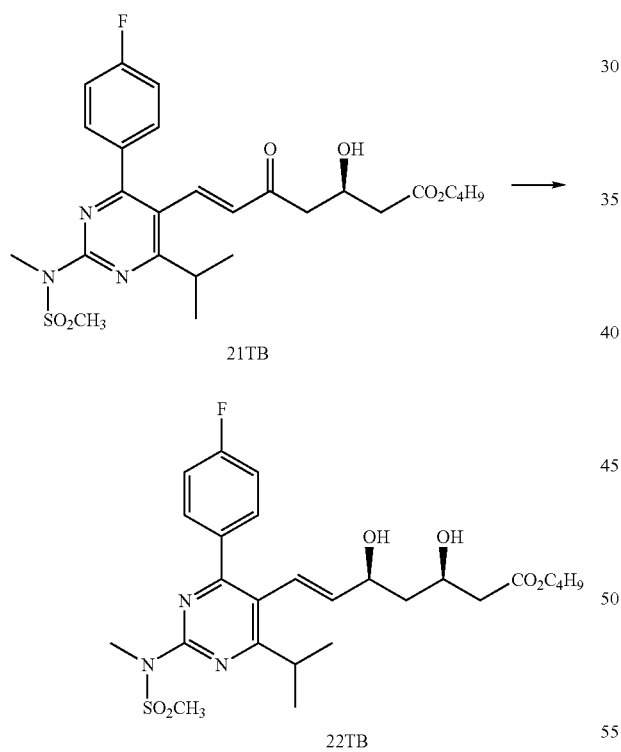

To a solution of 21TB (1 g) in dry THF (26 mL) and dry methanol (7 mL), a solution of diethylmethoxyborane (1M) in THF (2 mL) was added at about −78° C., forming a reaction mixture. The reaction mixture was stirred for 0.5 hour, $NaBH_4$ was added, and the stirring was continued for 3 hours. Acetic acid (1.2 mL) was added to the reaction mixture and the reaction mixture was warmed to ambient temperature.

Ethyl acetate (150 mL) was added to the reaction mixture and the pH was adjusted to 8 by addition of concentrated $NaHCO_3$ water solution. The layers were separated, and water was extracted by adding an additional amount of ethyl acetate (50 mL). The organic layers were combined and dried over $MgSO_4$. The solvents were then evaporated under reduced pressure, leaving a residue. The residue was treated with methanol and then the methanol was evaporated. Methanol treatment and evaporation was performed two more times, yielding crude Compound 22TB (TBRE) (0.87 g, 86%).

Example 16

Conversion of Compound 22TB into Rosuvastatin Ca with Extraction in Ethyl Acetate A 1 L reactor equipped with a mechanical stirrer was charged with EtOH (3 L), water (1800 mL), and TBRE (600 g), forming a reaction mixture. NaOH (47%, 1.2 eq, 114 g) was slowly added to the reaction mixture, at RT. The reaction mixture was stirred at about RT for two hours. The reaction mixture was filtered under reduced pressure with Synter and Hyflo to eliminate the small particles present. The reaction mixture was concentrated under reduced pressure at about 40° C. until half the volume of the reaction mixture remained.

Water (2000 mL) was added to the reaction mixture and the reaction mixture was stirred at about RT for 5 minutes. An aqueous phase and an organic phase formed. The phases were separated, and the aqueous phase was washed with ethyl acetate (3000 mL) and stirred at RT for half an hour. The organic phase was discarded.

The aqueous phase was concentrated under reduced pressure at about 40° C. until half the volume remained. Water (2800 mL) was added to the aqueous phase and the aqueous phase was stirred at about RT for 5 minutes. $CaCl_2$ (124 g) was added to the aqueous phase in portions over a period of about 10 minutes at a temperature of about RT. The aqueous phase was then stirred at about RT for about 1 hour, filtered, and washed with 1200 mL of water, yielding a powdery compound (491 g, 88%).

What is claimed is:

1. A compound of the formula:

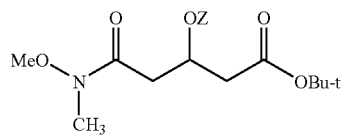

wherein Z is a hydroxy protecting group.

2. A compound of the formula:

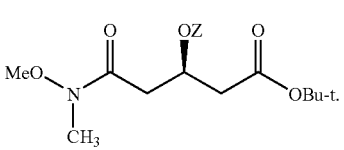

wherein Z is a hydroxy protecting group.

3. The compound of claims 1 or 2, wherein the compound has an enantiomeric purity of about 80% to about 98%.

4. The compound of claims 1 or 2, wherein the compound has an enantiomeric excess of about 85% to about 90%.

5. The compound of claims 1 or 2, wherein Z is a silyl group.

6. The compound of claims 1 or 2, wherein Z is a trialkylsilyl group having the formula-Si(A)$_3$ where each A is independently selected from a C$_1$-C$_6$ linear or branched aliphatic group and a C$_5$-C$_{12}$ aromatic group.

7. The compound of claims 1 or 2, wherein Z is selected from the group consisting of trimethylsilyl, triethylsilyl, triisopropylsilyl, tert-butyldiphenylsilyl, tert-butyldimethylsilyl, methyldiphenylsilyl, and dimethyiphenylsilyl.

8. The compounds of claims 1 or 2, wherein the compounds are isolated.

9. A process for preparing a compound of formula 2a, having the following structure:

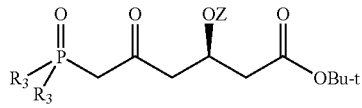

2a wherein R$_3$ is C$_1$ to C$_3$ alkyloxy; C$_5$-C$_{12}$aryloxy; C$_5$-C$_{12}$ aryloxy substituted with hydroxy, carboxyl, C$_1$-C$_4$ alkyl, C$_6$-C$_{12}$ alkoxy, C$_6$-C$_{12}$ aryl, C$_6$-C$_{12}$ arylalkyl, C$_6$-C$_{12}$ cycloalkyl or amino; and Z is a hydroxy protecting group comprising combining the compound of formula 9

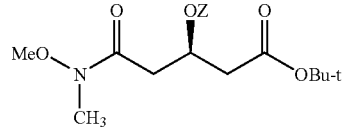

9 with a lithiated salt of a dialkyl phosphonate.

10. The process of claim 9, wherein the dialkyl phosphonate is a C$_1$-C$_3$dialkyl phosphonate.

11. The process of claim 9, wherein the reaction is carried out in toluene, xylene, cyclohexane, methyl t-butyl ether, tetrahydrofuran, or mixtures thereof.

12. The process of claim 9, wherein the reaction is carried out in methyl t-butyl ether or tetrahydrofuran.

13. A process for preparing a statin further comprising converting the compound obtained from claims 1 or 2 to the statin.

14. The process of claim 13, wherein the statin compound is selected from the group consisting of lovastatin, simvastatin, pravastatin, fluvastatin, cerivastatin, atorvastatin, rosuvastatin and pitavastatin.

15. The compound of claim 7, wherein Z is tert-butyldimethylsilyl.

* * * * *

UNITED STATES PATENT AND TRADEMARK OFFICE
CERTIFICATE OF CORRECTION

PATENT NO. : 7,687,660 B2
APPLICATION NO. : 12/148533
DATED : March 30, 2010
INVENTOR(S) : Vinod Kumar Kansal et al.

It is certified that error appears in the above-identified patent and that said Letters Patent is hereby corrected as shown below:

Column 34, line 18, change "tetrahydrofuran ,or" to -- tetrahydrofuran, or --

Signed and Sealed this

Eighth Day of June, 2010

David J. Kappos
*Director of the United States Patent and Trademark Office*